United States Patent
Park et al.

(10) Patent No.: US 9,267,903 B2
(45) Date of Patent: Feb. 23, 2016

(54) METHODS AND APPARATUSES FOR INSPECTING SEMICONDUCTOR DEVICES USING ELECTRON BEAMS

(71) Applicants: Mira Park, Suwon-si (KR); Younghoon Sohn, Incheon (KR); Yusin Yang, Seoul (KR); Sangkil Lee, Yongin-si (KR); Yong Deok Jeong, Hwaseong-si (KR)

(72) Inventors: Mira Park, Suwon-si (KR); Younghoon Sohn, Incheon (KR); Yusin Yang, Seoul (KR); Sangkil Lee, Yongin-si (KR); Yong Deok Jeong, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/015,204

(22) Filed: Aug. 30, 2013

(65) Prior Publication Data

US 2014/0061462 A1    Mar. 6, 2014

(30) Foreign Application Priority Data

Aug. 30, 2012   (KR) .................. 10-2012-0095593

(51) Int. Cl.
| | | |
|---|---|---|
| G01N 23/225 | (2006.01) | |
| H01J 37/28 | (2006.01) | |
| G01R 31/305 | (2006.01) | |

(52) U.S. Cl.
CPC .......... *G01N 23/2251* (2013.01); *G01R 31/305* (2013.01); *H01J 37/28* (2013.01); *H01J 2237/2806* (2013.01)

(58) Field of Classification Search
CPC ............. H01J 37/28; H01J 2237/2806; G01N 23/2251; G01R 31/305
See application file for complete search history.

(56) References Cited

U.S. PATENT DOCUMENTS

| | | | |
|---|---|---|---|
| 4,730,158 A | 3/1988 | Kasai et al. | |
| 6,172,363 B1 * | 1/2001 | Shinada ............... | G01R 31/305 250/307 |
| 6,344,750 B1 | 2/2002 | Lo et al. | |
| 6,366,688 B1 | 4/2002 | Jun et al. | |
| 6,525,318 B1 | 2/2003 | Kim et al. | |
| 6,566,897 B2 | 5/2003 | Lo et al. | |
| 6,730,908 B2 * | 5/2004 | Bigarre ............... | G01R 27/2617 250/306 |
| 6,859,060 B2 * | 2/2005 | Neo ..................... | G01R 31/307 257/E21.531 |
| 6,936,816 B2 | 8/2005 | Mankos et al. | |
| 7,132,301 B1 | 11/2006 | Fan | |
| 7,279,689 B2 | 10/2007 | Kadyshevitch et al. | |
| 7,655,906 B2 | 2/2010 | Cheng et al. | |
| 7,927,895 B1 | 4/2011 | Lavoie et al. | |
| 7,939,348 B2 | 5/2011 | Lim et al. | |
| 2001/0052781 A1 * | 12/2001 | Nozoe .................. | G01R 31/307 324/750.03 |
| 2003/0071646 A1 * | 4/2003 | Neo ..................... | G01R 31/307 324/754.22 |

(Continued)

FOREIGN PATENT DOCUMENTS

| | | |
|---|---|---|
| JP | 2000-046531 | 2/2000 |
| JP | 2001-284422 | 10/2001 |

(Continued)

*Primary Examiner* — Wyatt Stoffa
(74) *Attorney, Agent, or Firm* — Myers Bigel Sibley & Sajovec, P.A.

(57) ABSTRACT

Methods and apparatuses for inspecting a semiconductor device using electron beam are provided. The methods may include performing detection operations on a detection target pattern N times and determining a number of detection operations which have been performed until a maximum secondary electron amount of the detection target pattern is obtained. Each of the detection operations may include irradiating the detection target pattern with an electron beam, interrupting the irradiating and detecting a secondary electron amount of the detection target pattern after a detection waiting time has elapsed since the interrupting the irradiating.

24 Claims, 11 Drawing Sheets

(56) References Cited

U.S. PATENT DOCUMENTS

| | | | |
|---|---|---|---|
| 2003/0127593 A1* | 7/2003 | Shinada | H01J 37/29 250/310 |
| 2003/0179007 A1* | 9/2003 | Nozoe | G01R 31/307 324/754.22 |
| 2004/0061052 A1* | 4/2004 | Kim | H01J 37/266 250/307 |
| 2006/0076490 A1* | 4/2006 | Gunji | G01R 31/305 250/310 |
| 2007/0296447 A1 | 12/2007 | Bae et al. | |
| 2008/0237586 A1* | 10/2008 | Sun | H01L 22/32 257/48 |
| 2008/0296496 A1 | 12/2008 | Zhao et al. | |
| 2010/0239319 A1* | 9/2010 | Suhara | G03F 7/70675 399/169 |
| 2011/0220792 A1* | 9/2011 | Zewail | H01J 37/244 250/307 |
| 2012/0091339 A1* | 4/2012 | Ominami | H01J 37/28 250/307 |
| 2012/0153145 A1* | 6/2012 | Cheng | H01J 37/28 250/307 |

FOREIGN PATENT DOCUMENTS

| | | |
|---|---|---|
| JP | 2004-127431 | 4/2004 |
| KR | 1020000052614 | 8/2000 |
| KR | 100741858 | 7/2007 |
| KR | 1020070105201 | 10/2007 |
| KR | 1020090109708 | 10/2009 |
| KR | 1020090110629 | 10/2009 |

* cited by examiner

METHODS AND APPARATUSES FOR INSPECTING SEMICONDUCTOR DEVICES USING ELECTRON BEAMS

CROSS-REFERENCE TO RELATED APPLICATION

This U.S. non-provisional patent application claims priority under 35 U.S.C. §119 to Korean Patent Application No. 10-2012-0095593, filed on Aug. 30, 2012, in the Korean Intellectual Property Office, the disclosure of which is hereby incorporated by reference in its entirety.

FIELD

The present disclosure generally relates to the field of electronics, and more particularly, to inspection of semiconductor devices.

BACKGROUND

Semiconductor devices are widely used in electronic industries because of those small sizes, multi-function, and/or low manufacture costs. Semiconductor devices may include various patterns formed through various manufacturing processes such as deposition, photolithography, etch or ion implantation.

Inspection apparatuses, using electron beams, may be used to identify manufacturing defects in semiconductor devices.

SUMMARY

A method of inspecting a semiconductor device may include obtaining a reference electron-decay time of a reference pattern and performing detection operations on a detection target pattern N times. Each of the detection operations may include irradiating an electron beam to the detection target pattern, interrupting the electron beam and detecting a secondary electron amount of the detection target pattern at or after the reference electron-decay time has elapsed since the interrupting the electron beam. The method may also include determining a number of detection operations which have been performed until a maximum secondary electron amount of the detection target pattern is obtained.

In various embodiments, the method may further include obtaining an electron-decay time of the detection target pattern. The electron-decay time of the detection target pattern may be greater than the reference electron-decay time of the reference pattern, and a detection waiting time, which is a time interval between interrupting an electron beam and detecting a secondary electron amount of the detection target pattern in each of the detection operations, may be less than the electron-decay time of the detection target pattern.

In various embodiments, a time interval between detecting a secondary electron amount of the detection target pattern of an i-th detection operation and a start of irradiating an electron beam to the detection target pattern of an (i+1)-th detection operation may be less than a time interval between the electron-decay time of the detection target pattern and the detection waiting time.

In various embodiments, the detection waiting time may be equal to the reference electron-decay time.

According to various embodiments, obtaining the reference electron-decay time of the reference pattern may include irradiating an electron beam to the reference pattern, interrupting the electron beam, and continuously detecting a secondary electron amount of the reference pattern in real-time since a start of irradiating the electron beam.

In various embodiments, obtaining the reference electron-decay time of the reference pattern may further include determining the reference electron-decay time of the reference pattern as a time that has elapsed until the secondary electron amount of the reference pattern becomes substantially zero or a noise signal level after interrupting the electron beam.

According to various embodiments, obtaining the electron-decay time of the detection target pattern may include irradiating an electron beam to the detection target pattern, interrupting the electron beam and continuously detecting the secondary electron amount of the detection target pattern in real-time since a start of irradiating the electron beam.

According to various embodiments, obtaining the electron-decay time of the detection target pattern may further include determining the electron-decay time of the detection target pattern as a time that has elapsed until the secondary electron amount of the detection target pattern becomes substantially zero or a noise signal level after interrupting the electron beam.

In various embodiments, the reference pattern may be electrically connected to a first lower conductive pattern disposed between the reference pattern and a substrate and the detection target pattern may be electrically isolated from a second lower conductive pattern disposed between the detection target pattern and the substrate.

In various embodiments, the reference pattern may be an opened contact hole or a contact plug in the opened contact hole and the detection target pattern may be a not-opened contact hole or a contact plug in the not-opened contact hole.

According to various embodiments, performing detection operations on the detection target pattern N times may include performing scan processes N times on a frame region in a substrate. The frame region may include a plurality of pixel regions and one of the plurality of pixel regions may include the detection target pattern. Each of the scan processes may include detection operations on respective ones of the plurality of pixel regions.

In various embodiments, a scanning time interval between detecting a secondary electron amount of the one of the plurality of pixel regions of an i-th scan process and a start of irradiating an electron beam to the one of the plurality of pixel regions of an (i+1)-th scan process may less than a time interval between an electron-decay time of the detection target pattern and the reference electron-decay time. The electron-decay time of the detection target pattern may be a time that has elapsed until the secondary electron amount of the detection target pattern becomes substantially zero or a noise signal level since interrupting the electron beam.

According to various embodiments, the scanning time interval may include a frame movement time, an irradiation time obtained by multiplying a time during which an electron beam has been irradiated in each of the detection operations by a number of the pixel regions and a detection time obtained by multiplying the reference electron-decay time by the number of the pixel regions. The detection operations may be performed by an inspecting head and the frame movement time may be a movement time of the inspecting head.

In various embodiments, the plurality of pixel regions may be two-dimensionally arranged along rows and columns in the frame region when viewed from a plan perspective.

In various embodiments, the plurality of pixel regions may be arranged along one direction to constitute one row in the frame region when viewed from a plan perspective.

According to various embodiments, an (i+1)-th detection operation may be performed immediately after an i-th detection operation.

According to various embodiments, the method may further include performing detection operations on a pattern in a mass production substrate M times. M may be the determined number of detection operations which have been performed until the maximum secondary electron amount of the detection target pattern is obtained.

A semiconductor device inspecting apparatus may include a stage configured to receive a substrate including a detection target pattern. The apparatus may also include an inspecting head configured to perform detection operations on the detection target pattern N times. The inspecting head may include an electron beam irradiating part, which is configured to irradiate an electron beam to the detection target pattern and to interrupt the electron beam, and a detector, which is configured to detect a secondary electron amount of the detection target pattern at or after a reference electron-decay time has elapsed since interrupting the electron beam in each of the detection operations. The apparatus may further include a controller identifying a number of detection operations which have been performed until a maximum secondary electron amount of the detection target pattern is obtained.

A semiconductor device inspecting apparatus may include a stage configured to receive a substrate including a pattern. The apparatus may also include a detecting unit including an electron beam irradiating part, which is configured to irradiate an electron beam on the pattern and to interrupt the electron beam, and a detector, which is configured to continuously detect a secondary electron amount of the pattern. The apparatus may further include a controller configured to process data provided by the detecting unit.

A method of inspecting an integrated circuit (IC) device may include repetitively performing electron beam irradiation operations on a pattern in the IC device M times. Each of the electron beam irradiation operations may include irradiating the pattern with an electron beam for an irradiation time and interrupting the irradiating. The method may also include detecting a secondary electron amount of the pattern after a detection waiting time has elapsed since the repetitively performing the electron beam irradiation operations.

According to various embodiments, the method may further include determining a reference electron-decay time. The detection waiting time may be equal to or greater than the reference electron-decay time.

In various embodiments, determining the reference electron-decay time may include irradiating a reference pattern with the electron beam for the irradiation time, interrupting the irradiating after the irradiation time elapsed, continuously detecting a secondary electron amount of the reference pattern since a start of the irradiating and determining the reference electron-decay time as a time for the secondary electron amount of the reference pattern to become substantially zero or less than a magnitude of a noise signal after the interrupting the irradiating.

According to various embodiments, the method may further include determining an electron-decay time. The detection waiting time may be less than the electron-decay time.

In various embodiments, determining the electron-decay time may include irradiating a target pattern with the electron beam for the irradiation time, interrupting the irradiating after the irradiation time elapsed, continuously detecting a secondary electron amount of the target pattern since a start of the irradiating and determining the electron-decay time as a time for the secondary electron amount of the target pattern to become substantially zero or less than a magnitude of a noise signal after the interrupting the irradiating.

According to various embodiments, the method may further include repetitively performing detection operations on a target pattern to provide respective secondary electron amounts of the target pattern and determining M as a number of detection operations that have been performed when a maximum secondary electron amount of the target pattern is obtained. Each of the detection operations may include irradiating the target pattern with the electron beam, interrupting the irradiating and detecting a secondary electron amount of the target pattern at or after a reference electron-decay time has elapsed since the interrupting the irradiating.

A method of inspecting an integrated circuit (IC) device may include repetitively performing detection operations on a target pattern in a substrate to provide respective secondary electron amounts of the target pattern. Each of the detection operations may include irradiating the target pattern with an electron beam, interrupting the irradiating, and detecting a secondary electron amount of the target pattern after a detection waiting time has elapsed since the interrupting the irradiating. The method may also include determining a number of detection operations that have been performed when a maximum secondary electron amount of the target pattern is obtained.

According to various embodiments, the method may further include determining a reference electron-decay time. The detection waiting time may be equal to or greater than the reference electron-decay time.

In various embodiments, determining the reference electron-decay time may include irradiating a reference pattern with the electron beam for the irradiation time, interrupting the irradiating after the irradiation time elapsed, continuously detecting a secondary electron amount of the reference pattern since a start of the irradiating and determining the reference electron-decay time as a time for the secondary electron amount of the reference pattern to become substantially zero or less than a magnitude of a noise signal after the interrupting the irradiating.

According to various embodiments, the method may further include determining an electron-decay time. The detection waiting time may be less than the electron-decay time.

In various embodiments, determining the electron-decay time may include irradiating a target pattern with the electron beam for the irradiation time, interrupting the irradiating after the irradiation time elapsed, continuously detecting a secondary electron amount of the target pattern since a start of the irradiating and determining the electron-decay time as a time for the secondary electron amount of the target pattern to become substantially zero or less than a magnitude of a noise signal after the interrupting the irradiating.

In various embodiments, a time interval between detecting a secondary electron amount of the target pattern of an i-th detection operation and a start of irradiating an electron beam to the target pattern of an (i+1)-th detection operation may be less than a time interval between an electron-decay time and the detection waiting time. The method may further include determining the electron-decay time, which include irradiating a target pattern with the electron beam for the irradiation time, interrupting the irradiating after the irradiation time elapsed, continuously detecting a secondary electron amount of the target pattern since a start of the irradiating, and determining the electron-decay time as a time for the secondary electron amount of the target pattern to become substantially zero or less than a magnitude of a noise signal after the interrupting the irradiating.

DETAILED DESCRIPTION

Figure 1:
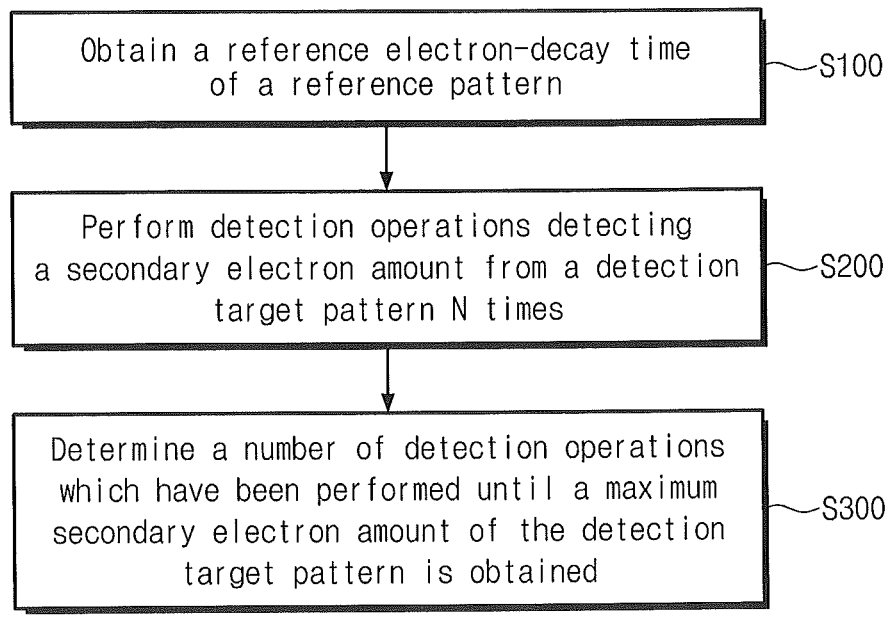
FIGS. 1 and 2 are flowcharts illustrating methods of inspecting semiconductor devices according to some embodiments of the inventive concept.

The inventive concept will now be described more fully hereinafter with reference to the accompanying drawings, in which exemplary embodiments of the inventive concept are shown. It should be noted, however, that the inventive concept is not limited to the following exemplary embodiments, and may be implemented in various forms. The exemplary embodiments are provided so that this disclosure will be thorough and complete, and will convey the scope of the disclosure to those skilled in the art. In the drawings, embodiments of the inventive concept are not limited to the specific examples provided herein and are exaggerated for clarity. Like reference numbers refer to like elements throughout.

The terminology used herein is for the purpose of describing particular embodiments only and is not intended to limit the invention. As used herein, the singular terms 'a,' 'an' and 'the' are intended to include the plural forms as well, unless the context clearly indicates otherwise. As used herein, the term 'and/or' includes any and all combinations of one or more of the associated listed items. It will be understood that when an element is referred to as being 'connected' or 'coupled' to another element, it may be directly connected or coupled to the other element or intervening elements may be present.

Similarly, it will be understood that when an element such as a layer, region or substrate is referred to as being 'on' another element, it can be directly on the other element or intervening elements may be present. In contrast, the term 'directly' means that there are no intervening elements. It will be further understood that the terms 'comprises', 'comprising,', 'includes' and/or 'including', when used herein, specify the presence of stated features, integers, steps, operations, elements, and/or components, but do not preclude the presence or addition of one or more other features, integers, steps, operations, elements, components, and/or groups thereof.

Additionally, exemplary embodiments in the detailed description will be described with sectional views and/or plan views as exemplary views of the inventive concept. Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concept explained and illustrated herein include their complementary counterparts.

Accordingly, aspects of the present disclosure may be implemented entirely hardware, entirely software (including firmware, resident software, micro-code, etc.) or combining software and hardware implementation that may all generally be referred to herein as a "circuit," "controller,", "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, assembly language, dynamic programming languages such as Python, Ruby and Groovy, or other programming languages.

As appreciated by the present inventors, conventional inspection methods using electron beams may not be reliable in inspecting small patterns for defects. Since amounts of secondary electrons detected from the small patterns can be small, an amount of secondary electrons from the pattern including a defect may be hardly distinguishable from an amount of secondary electrons associates with a pattern free of defects. Inspection methods according to various embodiments of the inventive concept, however, secondary electron amounts from a pattern including a defect may be accumulated through repetitive detection operations and thus the methods may be more reliable in identifying defects in small patterns.

Figure 2:
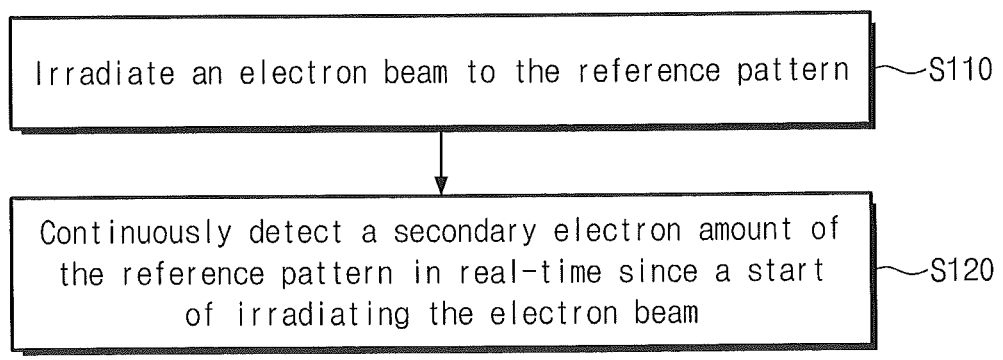
Figure 3:
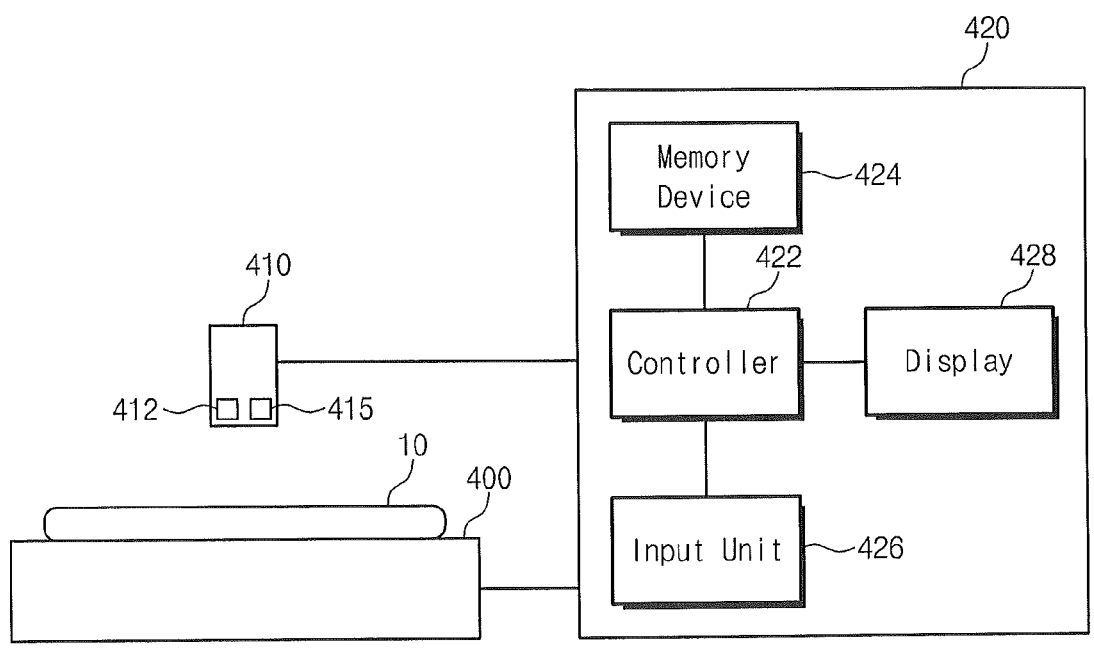
FIG. 3 is a schematic diagram illustrating a semiconductor device inspecting apparatus according to some embodiments of the inventive concept.
Figure 4:
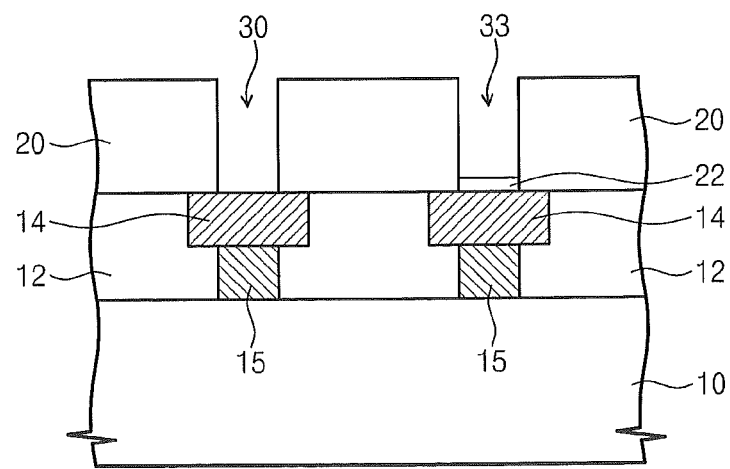
FIG. 4 is a cross-sectional view illustrating a reference pattern and a detection target pattern according to some embodiments of the inventive concept.
Figure 5:
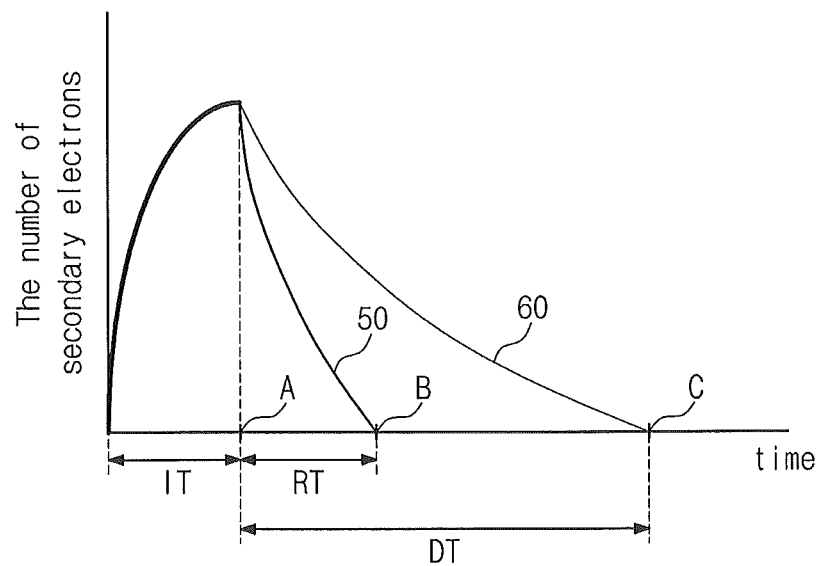
FIG. 5 is a graph illustrating electron-decay times of a reference pattern and a detection target pattern according to some embodiments of the inventive concept.

FIGS. 1 and 2 are flowcharts illustrating methods of inspecting semiconductor devices according to some embodiments of the inventive concept. FIG. 3 is a schematic diagram illustrating a semiconductor device inspecting apparatus according to some embodiments of the inventive concept. FIG. 4 is a cross-sectional view illustrating a reference pattern and a detection target pattern according to some embodiments of the inventive concept. FIG. 5 is a graph illustrating electron-decay times of a reference pattern and a detection target pattern according to some embodiments of the inventive concept.

Referring to FIGS. 1 and 4, a reference electron-decay time of a reference pattern 30 is obtained (S100). As illustrated in FIG. 4, the reference pattern 30 may be formed on a substrate 10. The reference pattern 30 is included in a semiconductor device. The reference pattern 30 may be connected to a lower conductive pattern 14 thereunder. The reference pattern 30 has a normal shape. In other words, the reference pattern 30 is a pattern capable of normally performing a desired operation (e.g., electrical connection) thereof. In some embodiments, the reference pattern 30 may be a normally opened contact hole exposing the lower conductive pattern 14, as illustrated in FIG. 4. In more detail, the reference pattern 30 may penetrate an interlayer insulating layer 20 covering to the lower conductive pattern 14, so as to expose the lower conductive pattern 14. The lower conductive pattern 14 may be electrically connected to the substrate 10. The lower conductive pattern 14 may be disposed in a lower insulating layer 12, and a lower plug 15 may penetrate the lower insulating layer 12 disposed between the lower conductive pattern 14 and the substrate 10. In this case, the lower conductive pattern 14 may be electrically connected to the substrate 10 through the lower plug 15. Alternatively, the lower conductive pattern 14 may be in contact with the substrate 10 or may be a portion of the substrate 10.

The substrate 10 may be a wafer including a plurality of chip regions. The semiconductor device may be formed in each of the chip regions. In other words, the reference pattern 30 may be one of a plurality of patterns formed in each of the chip regions. The reference pattern 30 may be confirmed in advance by at least one of various methods (e.g., a method using a scanning electron microscope (SEM)).

An electron beam may be irradiated to the reference pattern 30, so that secondary electrons may be generated from the reference pattern 30. The reference electron-decay time may correspond to a time for the secondary electrons of the reference pattern 30 to become substantially zero after interrupting the electron beam. The secondary electrons may become substantially zero during the reference electron-decay time of the reference pattern 30. The step S100 of obtaining the reference electron-decay time may include steps S110 and S120 of FIG. 2. The step S100 will be described in more detail with reference to FIGS. 1 to 5.

A semiconductor device inspecting apparatus according to some embodiments of the inventive concept will be described with reference to FIG. 3. Referring to FIG. 3, the semiconductor device inspecting apparatus may include a stage 400 on which the substrate 10 is loaded, an inspecting head 410 disposed over the stage 400, and an electronic system 420 controlling the inspecting head 410.

The inspecting head 410 may include an electron beam irradiating part 412 and a detector 415. The electron beam irradiating part 412 may irradiate the electron beam to the substrate 100. In particular, the electron beam irradiating part 412 may irradiate the electron beam to a pixel region of the substrate 10. The pixel region may include at least one pattern. The detector 415 may detect the amount of secondary electrons emitted from the substrate 10. Hereinafter, the amount of secondary electrons is defined as 'a secondary electron amount'. The detector 415 may detect a secondary electron amount of the reference pattern 30. The inspecting head 410 may be controlled by the electronic system 420. For example, the electronic system 420 may control operations of the electron beam irradiating part 412, operations of the detector 415, movement of the inspecting head 410, and may process data obtained from the inspecting head 410.

The electronic system 420 may include a controller 422, a memory device 424, an input unit 426, and a display 428. The controller 422 may control the operations of the electron beam irradiating part 412 (e.g., electron beam irradiation and electron beam interruption). Additionally, the controller 422 may control the operations of the detector 412 (e.g., detection of the secondary electron amount). Furthermore, the controller 422 may process the data obtained from the inspecting head 410 in various forms such as numerical values, a graph, gray levels, and/or an image. The controller 422 may store the data obtained from the inspecting head 410 and/or data processed by the controller 422 in the memory device 424. The memory device 424 may further store commands for performing the control functions of the controller 422. The input unit 426 may include at least one of various input tools such as a keyboard, a keypad, and/or a stick type input tool. The display 428 may display the data stored in the memory device 424 and/or the data processed by the controller 422. The display 428 may display the data in various forms such as numerical values, gray levels, a graph, and/or an image.

In some embodiments, the detector 415 may continuously detect the secondary electron amount in real-time, and the controller 422 may control the real-time detection of the detector 415. The controller 422 may store the secondary electron amount detected in real-time in the memory device 424 and/or may display the secondary electron amount detected in real-time at the display 428. The secondary electron amount detected in real-time may be displayed in various forms such as a graph, numerical values, a table, and/or gray levels.

The step S100 of obtaining the reference electron-decay time may be performed using the semiconductor device inspecting apparatus described above.

Referring to FIGS. 1 to 5, the substrate 10 including the reference pattern 30 may be loaded on the stage 400. The inspecting head 410 may be located over the reference pattern 30. As illustrated in FIG. 2, the electron beam irradiating part 412 irradiates the electron beam to the reference pattern 30 (S110). The detector 415 continuously detects the secondary electron amount of the reference pattern 30 in real-time since a start of irradiating the electron beam, thereby obtaining the reference electrode-decay time RT (S120). Thus, a first curved line 50 of a graph in FIG. 5 may be obtained. The first curved line 50 shows the number of the secondary electrons of the reference pattern 30 according to a time.

In more detail, the electron beam irradiating part 412 may irradiate the electron beam for an irradiation time IT. The electron beam may be interrupted at a first point A of time. The irradiation time IT may be a time interval between the start of the irradiating the electron beam and the first point A of time.

The detector 415 may continuously detect the secondary electron amount of the reference pattern 30 in real-time since the start of the irradiating the electron beam. In some embodiments, the detector 415 may be operated in advance of the start of the irradiation the electron beam so as to continuously detect the secondary electron amount of the reference pattern 30 in real-time.

The detected secondary electron amount of the reference 30 may have the maximum value at the first point A of time. As illustrated in the first curved line 50 of FIG. 5, the secondary electron amount of the reference pattern 30 may be reduced from the first point A of time. A variation of the secondary electron amount of the reference pattern 30 may become substantially zero at a second point B of time. The reference electron-decay time RT corresponds to a time from the first point A of time to the second point B of time. In other words, the reference electron-decay time RT is the time from the first point A of time at which the secondary electron amount of the reference pattern 30 has the maximum value to the second point B of time at which the variation of the secondary electron amount of the reference pattern 30 becomes substantially zero.

After the irradiation of the electron beam is interrupted, the secondary electrons of the reference pattern 30 may be discharged through the lower conductive pattern 14 thereunder. Thus, the secondary electron amount of the reference pattern 30 may begin to be reduced from the first point A of time. In some embodiments, the detected secondary electron amount of the reference pattern 30 may become substantially zero after the second point B of time. In other words, the amount of the secondary electrons generated by the electron beam may become substantially zero at the second point B of time. In some embodiments, a noise signal may be detected from the reference pattern 30 after the second point B of time.

The controller 422 may process data of the secondary electron amount of the reference pattern 30 detected by the detector 415 and then may display the graph of FIG. 5 (e.g., the first curved line 50, the first and second points A and B of time, the irradiation time IT, and the reference electron-decay time RT) on the display 428. Additionally, the controller 422 may store the secondary electron amount of the reference pattern 30 detected by the detector 415 in the memory device 424.

As described above, the reference electron-decay time RT of the reference pattern 30 may be obtained using the semiconductor device inspecting apparatus (S100).

As illustrated in FIG. 4, a detection target pattern 33 may be disposed on the substrate 10. The detection target pattern 33 has a different shape from the reference pattern 30. The detection target pattern 33 has an abnormal shape. The detection target pattern 33 does not normally perform a desired operation thereof. In other words, the detection target pattern 33 corresponds to a bad pattern. In some embodiments, the detection target pattern 33 may be a not-opened contact hole not exposing a lower conductive pattern 14 thereunder, as illustrated in FIG. 4. In some embodiments, a residue 22 may remain on the lower conductive pattern 15 under the detection target pattern 33. The residue 22 may be a portion of the interlayer insulating layer 20 and/or an etch by-product. The detection target pattern 33 may not expose the lower conductive pattern 14 due to the residue 22. The detection target pattern 33 may be included in the substrate 10 having the reference pattern 30. Alternatively, the detection target pattern 33 and the reference pattern 30 may be included in different substrates. The detection target pattern 33 may be confirmed in advance by at least one of various methods (e.g., a method using a SEM).

If the electron beam is irradiated to the detection target pattern 33, secondary electrons may be generated in the detection target pattern 33. The secondary electrons of the detection target pattern 33 may be discharged through the lower conductive pattern 14 under the detection target pattern 33. However, a discharging speed of the secondary electrons of the detection target pattern 33 may be reduced significantly due to the residue 22.

An electron-decay time of the detection target pattern 33 may be obtained using the semiconductor device inspecting apparatus illustrated in FIG. 3.

Referring to FIGS. 3 to 5, the electron beam irradiating part 412 may irradiate the electron beam to the detection target pattern 33. Also, the detector 415 may continuously detect the secondary electrons of the detection target pattern 33 in real-time. Thus, a second curved line 60 of FIG. 5 may be obtained. The second curved line 60 shows the number of the secondary electrons of the detection target pattern 33.

In more detail, the electron beam irradiating part 412 may irradiate the electron beam to the detection target pattern 33 for the irradiation time IT and then may interrupt the electron beam at the first point A of time. The secondary electron amount of the detection target pattern 33 begins to be reduced from the first point A of time. A variation of the secondary electron amount of the detection target pattern 33 may become substantially zero at a third point C of time. The electron-decay time DT of the detection target pattern 33 corresponds to a time interval between the first point A and the third point C. Since the discharging speed of the secondary electrons of the detection target pattern 33 through the lower conductive pattern 14 is significantly reduced due to the residue 22, the electron-decay time DT of the detection target pattern 33 may be greater than the reference electron-decay time RT of the reference pattern 30. The secondary electrons may not be detected from the reference pattern 30 or only a noise signal may be detected from the reference pattern 30 immediately after the reference electron-decay time RT (i.e., immediately after the second point B of time). On the contrary, a secondary electron amount may be detected from the detection target pattern 33 immediately after the second point B of time. In other words, the secondary electron amount of the reference pattern 30 generated by the electron beam may become substantially zero at the second point B of time, but some of the secondary electrons of the detection target pattern 33 generated by the electron beam may be accumulated in the detection target pattern 33. Thus, the detected secondary electron amount of the detection target pattern 33 may be greater than the detected secondary electron amount of the reference pattern 30 at the second point B of time.

In some embodiments, the reference pattern 30 and the detection target pattern 33 may be the opened contact hole and the not-opened contact hole, respectively. However, the inventive concept is not limited thereto.

Figure 6:
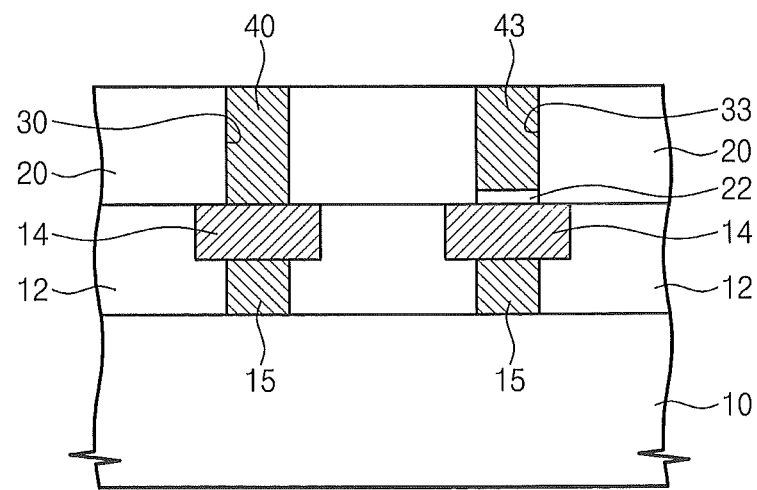
FIG. 6 is a cross-sectional view illustrating a reference pattern and a detection target pattern according to some embodiments of the inventive concept.

FIG. 6 is a cross-sectional view illustrating a reference pattern and a detection target pattern according to some embodiments of the inventive concept.

Referring to FIG. 6, a reference pattern 40 may be a contact plug disposed in an opened contact hole 30. The reference pattern 40 may be connected to a lower conductive pattern 14 under the reference pattern 40 due to the opened contact hole 30. In other words, the reference pattern 40 may be a normal contact plug. A detection target pattern 43 may be a contact plug disposed in a not-opened contact hole 33. The detection target pattern 43 may not be in contact with a lower conductive pattern 14 under the not-opened contact hole 33 because of the residue 22. In other words, the detection target pattern 43 may be an abnormal contact plug not contacting the lower conductive pattern 14 thereunder.

However, the inventive concept is not limited thereto. The reference pattern may be one of various normal patterns which is connected to the lower conductive pattern, and the detection target pattern may be one of various abnormal patterns which may not be connected to the lower conductive pattern. Hereinafter, the reference pattern 30 (e.g., the opened contact hole) and the detection target pattern 33 (e.g., the not-opened contact hole) of FIG. 4 will be described as examples for the purpose of ease and convenience in explanation.

Referring again to FIG. 1, after the reference electron-decay time is obtained (S100), detection operations detecting the secondary electron amount from the detection target pattern 33 are repeatedly performed N times, where 'N' denotes a natural number equal to or greater than 2 (S200). In other words, the detection operations are repeatedly performed on one detection target pattern 33. Each of the detection operations may be performed as described in a flowchart of FIG. 7. The step S200 will be described in more detail with reference to FIGS. 7 and 8.

Figure 7:
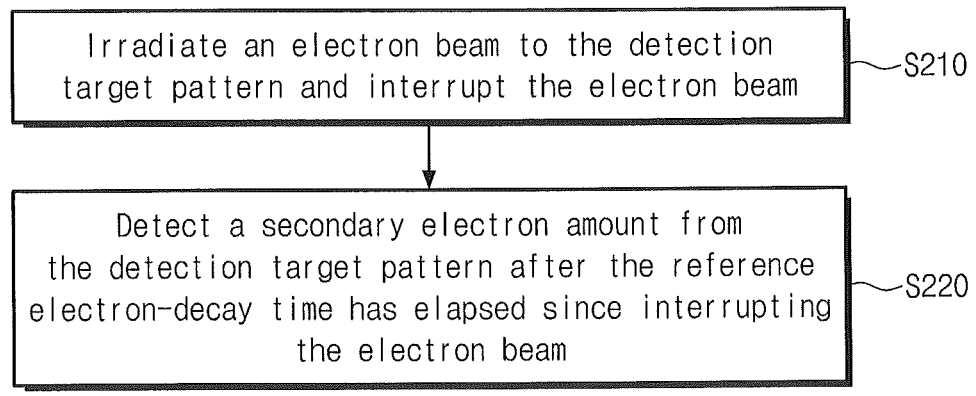
FIG. 7 is a flowchart illustrating a detecting operation according to some embodiments of the inventive concept.
Figure 8:
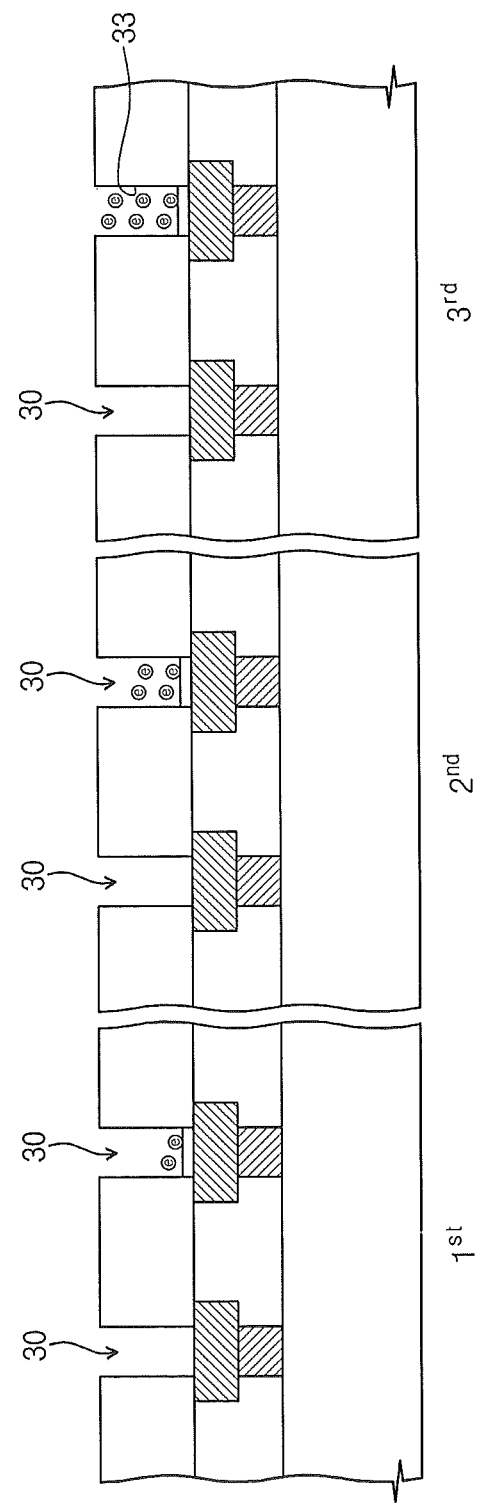
FIG. 8 a cross-sectional view illustrating variation of secondary electrons in a reference pattern and a detection target pattern according to some embodiments of the inventive concept.

FIG. 7 is a flowchart illustrating a detecting operation according to some embodiments of the inventive concept. FIG. 8 a cross-sectional view illustrating variation of secondary electrons in a reference pattern and a detection target pattern according to some embodiments of the inventive concept.

Referring to FIGS. 1, 4, and 7, the detection operation of the step S200 may include irradiating an electron beam to the detection target pattern 33 and interrupting the irradiating the electron beam (S210) and detecting the secondary electron amount from the detection target pattern 33 after the reference electron-decay time RT (S220) has elapsed since the interrupting the electron beam.

In some embodiments, the step S200 performing the detection operation N times may be performed using the semiconductor device inspecting apparatus of FIG. 3 or an inspecting apparatus similar to the semiconductor device inspecting apparatus of FIG. 3. Hereinafter, the step S200 performed by the semiconductor device inspecting apparatus of FIG. 3 will be described as an example for the purpose of ease and convenience in explanation.

Referring to FIGS. 1, 3, 4, 5, and 7, the substrate 10 including the detection target pattern 33 may be loaded on the stage 400, and then the inspecting head 410 may be located over the detection target pattern 33. The electron beam irradiating part 412 may irradiate the electron beam to the detection target pattern 33 and may interrupt the electron beam (S210). After electron beam is interrupted, the detector 415 may detect the secondary electron amount of the detection target pattern 33 after the reference electron-decay time RT has elapsed since the electron beam is interrupted (S220). The step S220 may be performed before the electron-decay time DT of the detection target pattern 33 elapsed. Thus, the secondary electrons of the detection target pattern 33 may not be completely discharged through the lower conductive pattern 14 when the detection operation is performed. As a result, some of the secondary electrons generated by the detection operation may be accumulated in the detection target pattern 33, and the accumulated secondary electrons may be detected in the step S220. In the step S220, a time interval between the interruption of the electron beam and a detecting point of time at which the secondary electron amount is detected is defined as a detection waiting time. The detection waiting time may be equal to or greater than the reference electron-decay time RT and less than the electron-decay time DT of the detection target pattern 33.

In the step S200, the detection operations including the step S210 and the step S220 are repeatedly performed N times on the detection target pattern 33, where 'N' denotes a natural number equal to or greater than 2. At this time, a time interval between an i-th detection operation and an (i+1)-th detection operation of the N times of detection operations (where 'i' denotes a natural number equal to or greater than 1 and equal to or less than N−1) may be less than a time interval between the detection waiting time and the electron-decay time DT of the detection target pattern 33. The time interval between an i-th detection operation and an (i+1)-th detection operation is a time interval between detecting a secondary electron amount of the detection target pattern 33 of an i-th detection operation and a start of irradiating an electron beam to the detection target pattern 33 of an (i+1)-th detection operation. Thus, as a number of the detection operation performed increases, the secondary electrons accumulated in the detection target pattern 33 may increase. For example, as illustrated in FIG. 8, some of the secondary electrons generated by a first detection operation may be accumulated in the detection target pattern 33, some of the secondary electrons generated by a second detection operation may also be accumulated in the detection target pattern 33, and then some of the secondary electrons generated of a third detection operation may be further accumulated in the detection target pattern 33. Thus, the secondary electron amount of the detection target pattern 33 detected by the third detection operation may be greater than the secondary electron amount of the detection target pattern 33 detected by the first detection operation.

As described above, the secondary electron amount is detected after the reference electron-decay time RT has elapsed since the electron beam is interrupted in the step S220 of the detection operation. Thus, if the detection operation is performed on the reference pattern 30, the secondary electrons of the reference pattern 30 may be substantially completely discharged through the lower conductive pattern 14, as illustrated in FIG. 8. In other words, even though the detection operation is repeatedly performed N times on the reference pattern 30, the secondary electron amount of the reference pattern 30 detected by a N-th detection operation may be substantially equal to the secondary electron amount of the reference pattern 30 detected by a first detection operation.

In some embodiments, the secondary electron amount of the detection target pattern 33 may be detected immediately after the reference electron-decay time RT has elapsed since the electron beam is interrupted in the step S220 of each of the detection operations. In other words, the detection waiting time may be equal to the reference electron-decay time RT. In this case, the time interval between the i-th detection operation and the (i+1)-th detection operation of the N times of detection operations may be less than a time interval between the reference electron-decay time RT and the electron-decay time DT of the detection target pattern 33.

Figure 9:
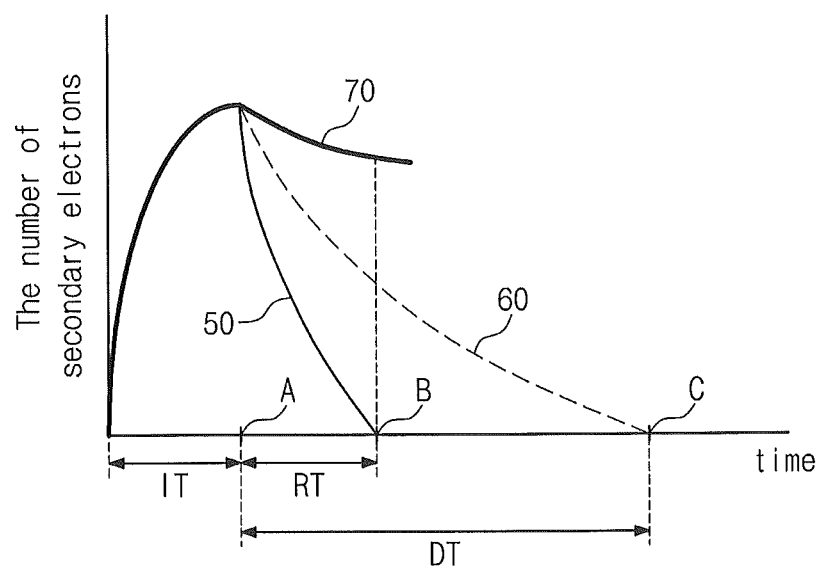
FIG. 9 is a graph illustrating electron-decay times of a reference pattern and a detection target pattern according to some embodiments of the inventive concept.

FIG. 9 is a graph illustrating electron-decay times of a reference pattern and a detection target pattern according to some embodiments of the inventive concept.

Referring to FIGS. 1, 7, 8, and 9, a third curved line 70 of FIG. 9 represents the secondary electron amount detected after the detection operation 33 is repeatedly performed a plurality of times on the detection target pattern 33. As described above, the secondary electrons may be additionally accumulated in the detection target pattern 33 by the plurality of the detection operations. On the other hand, if the detection operations are performed on the reference pattern 30, the secondary electron amounts detected from the reference pattern 30 may be substantially same. Thus, after the detection operations are repeatedly performed, the difference between the secondary electron amount of the reference pattern 30 and the secondary electron amount of the detection target pattern 33 detected at the second point B of time may increase, as illustrated in FIG. 9.

As a result, the detection target pattern 33 may be more clearly distinguished from the reference pattern 30. Thus, it is possible to improve reliability of the method of inspecting the detection target pattern 33.

The detection target pattern 33 has a limited size. Thus, after predetermined times of the detection operations are performed, the secondary electrons accumulated in the detection target pattern 33 may be saturated or reduced. In other words, after the predetermined times of the detection operations, the secondary electrons may not be further accumulated due to a secondary electron-capacity limit of the detection target pattern 33 and/or a repulsive force between the accumulated secondary electrons. This will be described later in more detail.

In some embodiments, the step S200 may be performed using a frame region including a plurality of pixel regions. This will be mentioned in more detail with reference to FIGS. 10 and 11.

Figure 10:
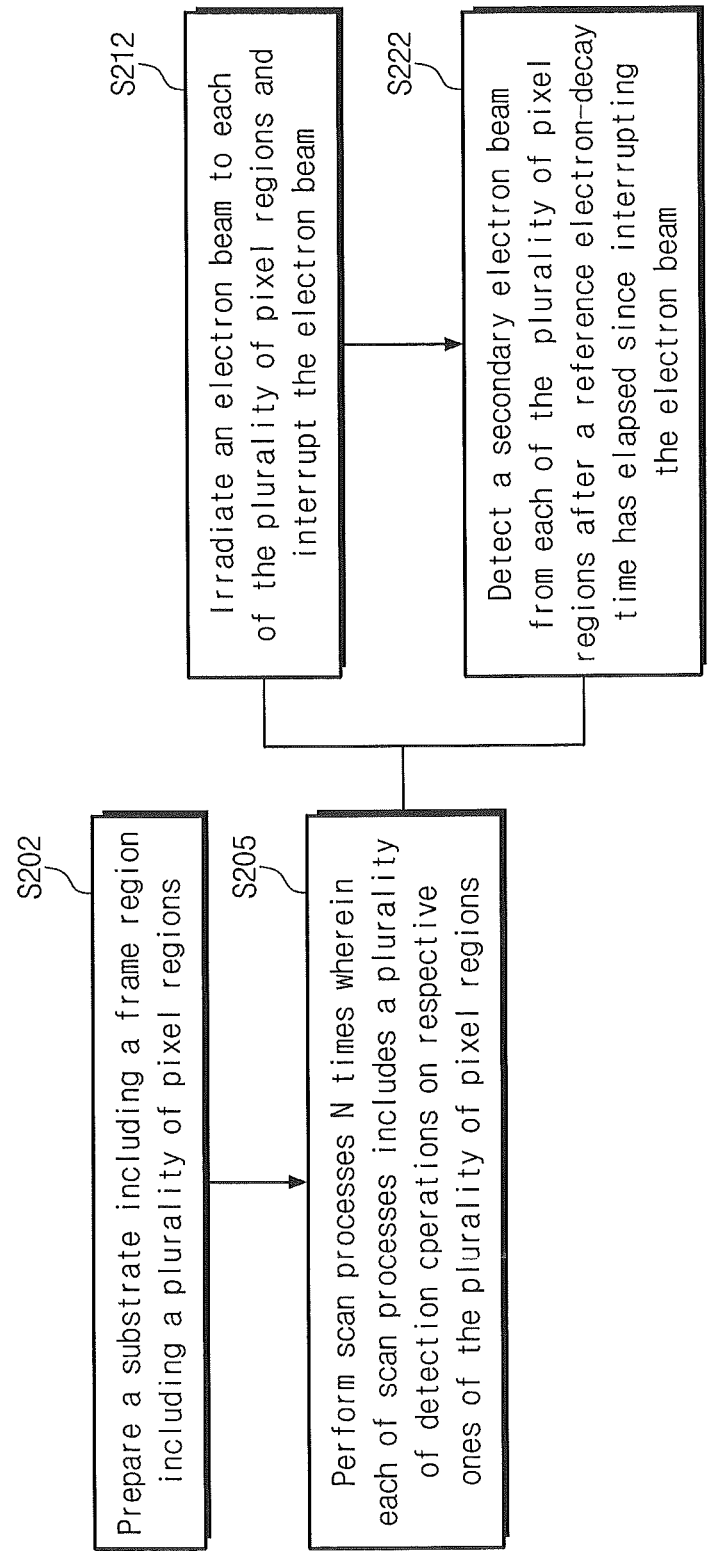
FIG. 10 is a flowchart illustrating a detecting operation according to some embodiments of the inventive concept.
Figure 11:
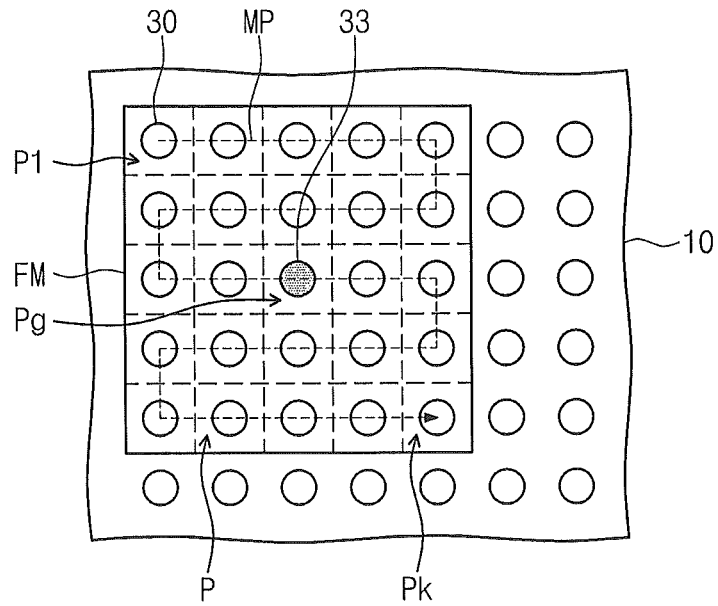
FIGS. 11 and 12 are plan views illustrating frame regions according to some embodiments of the inventive concept.

FIG. 10 is a flowchart illustrating a detecting operation according to some embodiments of the inventive concept. FIG. 11 is a plan view illustrating a frame region according to some embodiments of the inventive concept.

Referring to FIGS. 1, 3, 5, 10, and 11, the substrate 10 including a frame region FM may be prepared (S202). The frame region FM may have a plurality of pixel regions P1, P, Pg, and Pk. At least one pattern 30 and/or 33 may be disposed in each of the pixel regions P1, P, Pg, and Pk. Thus, a plurality of patterns 30 and 33 may be disposed in the frame region FM. In some embodiments, each of the pixel regions P1, P, Pg, and Pk may include one pattern, as illustrated in FIG. 11. However, the inventive concept is not limited thereto.

In some embodiments, the plurality of pixel regions P1, P, Pg, and Pk of the frame region FM may be two-dimensionally arranged along rows and columns when viewed from a plan perspective, as illustrated in FIG. 11.

The substrate 10 including the frame region FM may be loaded on the stage 400 of the semiconductor device inspecting apparatus. The inspecting head 410 may perform the detection operation on each of the pixel regions P1, P, Pg, and Pk. The inspecting head 410 may perform N times of scan processes on the frame region FM. Each of the scan processes may include a plurality of the detection operations performed on respective ones of the plurality of pixel regions P1, P, Pg, and Pk. The detection operations of the scan process may be performed along a movement path MP from a first pixel region P1 to the last pixel region Pk. In other words, the inspecting head 410 may move along the movement path MP. In some embodiments, if the pixel regions P1, P, Pg, and Pk are two-dimensionally arranged in the rows and columns as illustrated in FIG. 11, the movement path MP may have a zigzag form when viewed from a plan perspective. However, the inventive concept is not limited thereto.

Each of the detection operations included in each of the scan processes may include irradiating the electron beam to each of the pixel regions P1, P, Pg, and Pk and interrupting the electron beam (S212) and detecting a secondary electron amount of each of the pixel regions P1, P, Pg, and Pk immediately after the reference electron-decay time RT (S222) has elapsed since the electron beam is interrupted.

As described above, since the scan process is repeatedly performed N times, the detection operation may be performed N times on each of the pixel regions P1, P, Pg, and Pk. For example, the detection operation is performed N times on a g-th pixel region Pg including the detection target pattern 33.

If the number of the pixel regions in the frame region FM is k, a time interval between the detection operation of an i-th scan process and the detection operation of an (i+1)-th scan process performed on the g-th pixel region Pg may include a frame movement time Ft of the inspecting head 410, a value obtained by multiplying the irradiating time IT by the number k of the pixel regions, and a value obtained by multiplying the reference electron-decay time RT by the number k of the pixel regions. Here, 'i' denotes a natural number equal to or greater than 1 and equal to or less than N−1. The frame movement time Ft of the inspecting head 410 may be a movement time of the inspecting head 410 from the g-th pixel region Pg of the i-th scan process to the g-th pixel region Pg of the (i+1)-th scan process. The frame movement time Ft may be expressed by the following equation 1.

$$Ft=(k-1)\times Bt+Et \quad \text{[Equation 1]}$$

In the equation 1, 'k' denotes the number of pixel regions in the frame region FM, 'Bt' denotes a movement time of the inspecting head 410 between a pair of the pixel regions adjacent to each other, and 'Et' denotes a movement time of the inspecting head 410 from the last pixel region Pk to the first pixel region P1. In some embodiments, since the pixels regions are two-dimensionally arranged long rows and columns, 'k' (i.e., the number of the pixel regions in the frame region FM) denotes a natural number equal to or greater than 4. However, the inventive concept is not limited thereto.

In some embodiments, a time interval between the detection operation of the i-th scan process and the detection operation of the (i+1)-th scan process performed on the g-th pixel region Pg may be less than a time interval between the reference electron-decay time RT and the electron-decay time DT of the detection target pattern 33. The time interval between the detection operation of the i-th scan process and the detection operation of the (i+1)-th scan process performed on the g-th pixel region Pg is a time interval between detecting a secondary electron amount of the g-th pixel region of an i-th scan process and a start of irradiating an electron beam to the g-th pixel region of an (i+1)-th scan process. Thus, some of the secondary electrons of the detection target pattern 33 generated by the i-th scan process may be included in the secondary electron amount of the detection target pattern 33 detected in the (i+1)-th scan process.

The scan processes are repeatedly performed N times, so that it is possible to find a condition that a difference between the secondary electron amount of the reference pattern 30 and the secondary electron amount of the detection target pattern 33 is maximized.

The pixel regions P1, P, Pg, Pk in the aforementioned frame region FM are two-dimensionally arranged in the rows and the columns. Alternatively, the pixel regions may be arranged in other forms.

Figure 12:
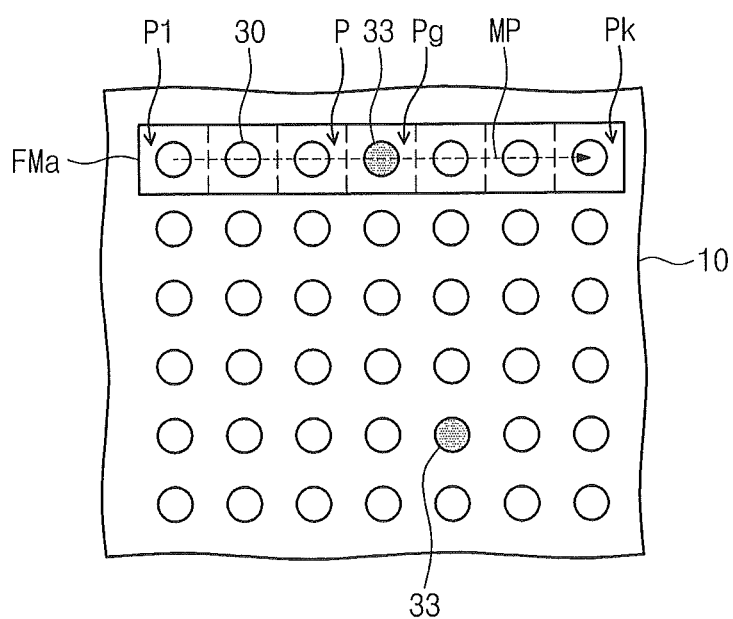

FIG. 12 is a plan view illustrating a frame region according to some embodiments of the inventive concept.

Referring to FIG. 12, a frame region FMa may include a plurality of pixel regions P1, P, Pg, and Pk, and the plurality of pixel regions P1, P, Pg, and Pk may be arranged along one direction to constitute one row. In other words, the pixel regions P1, P, Pg, and Pk in the frame region FMa may be linearly arranged. In this case, a movement path MP of the inspecting head 410 may be a linear shape extending in the one direction.

Figure 13:
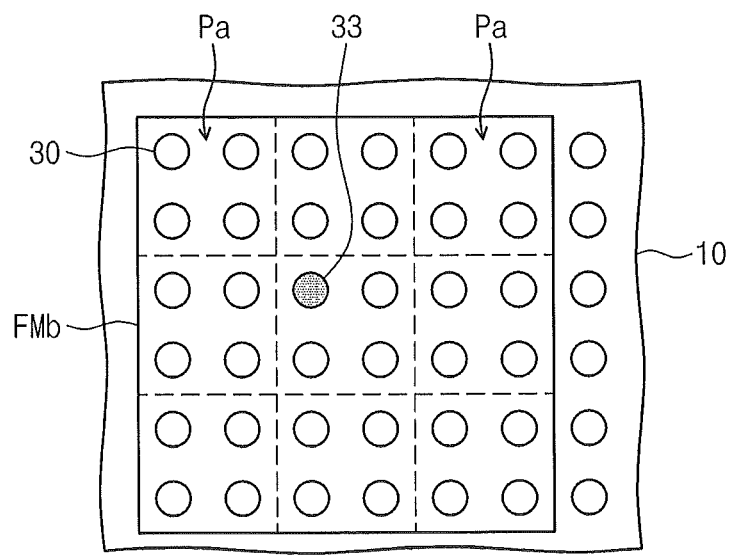
FIG. 13 is a plan view illustrating a pixel region according to some embodiments of the inventive concept.

As described above, each of the pixel regions P 1, P, Pg, and Pk in FIG. 11 may include one pattern 30 or 33. Alternatively, a plurality of patterns 30 and/or 33 may be disposed in each of pixel regions Pa in a frame region FMb, as illustrated in FIG. 13. The pixel region Pa including the plurality of patterns 30 and/or 33 may be applied to the frame region FMa of FIG. 12.

In some embodiments, the frame region FM may have one pixel region. The step S200 of FIG. 1 according to this embodiment will be described in detail with reference to FIGS. 14 and 15.

Figure 14:
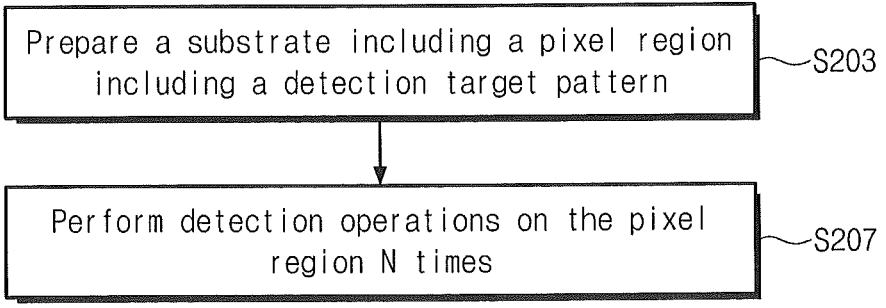
FIG. 14 is a flowchart illustrating a detecting operation according to some embodiments of the inventive concept.
Figure 15:
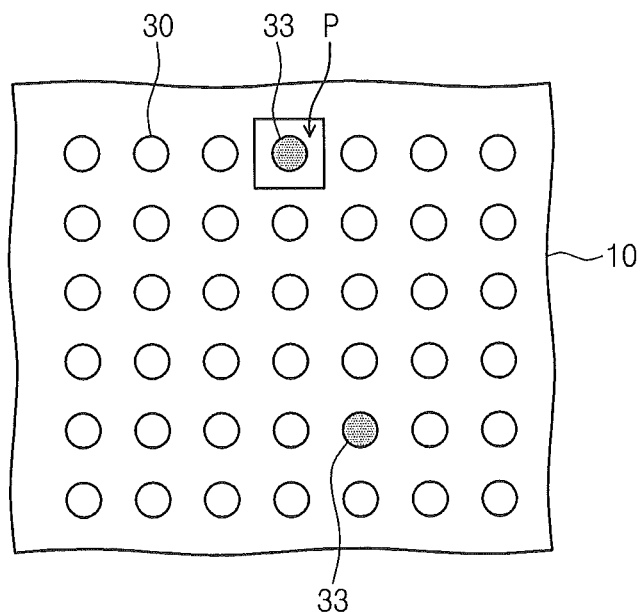
FIG. 15 is a plan view illustrating a pixel region according to some embodiments of the inventive concept.

FIG. 14 is a flowchart illustrating a detecting operation according to some embodiments of the inventive concept.

Referring to FIGS. 1, 3, 14, and 15, a substrate 10 including at least a pixel region P including the detection target pattern 33 is prepared (S203). The substrate 10 may be loaded on the stage 400 of the semiconductor device inspecting apparatus and then the inspecting head 410 may be located over the pixel region P having the detection target pattern 33. The detection operations may be continuously performed N times on the pixel region P by the inspecting head 410 (S207).

In the N times of the detection operations, an (i+1)-th detection operation may be performed immediately after an i-th detection operation. In other words, immediately after the i-th detection operation is performed on the detection target pattern 33, the electron beam of the (i+1)-th detection operation may be irradiated to the detection target pattern 33 and then the secondary electron amount of the detection target pattern 33 in the (i+1)-th detection operation may be detected immediately after the reference electron-decay time has elapsed since the electron beam is interrupted.

According to some embodiments, since the (i+1)-th detection operation is performed immediately after the i-th detection operation, the amount of the secondary electrons accumulated in the detection target pattern 33 may be maximized. Thus, it is possible to reduce a time required for maximizing the difference between the secondary electron amount of the reference pattern 30 and the secondary electron amount of the detection target pattern 33. As a result, an inspecting time of the semiconductor device inspecting method may be reduced.

Referring again to FIG. 1, after the step S200 is performed, a number of detection operations, which have been performed until a maximum secondary electron amount of the detection target pattern is obtained, may be determined from the secondary electron amounts of the detection target pattern 33 detected by the N times of the detection operations (S300). The controller 422 of the semiconductor device inspecting apparatus may determine the number of detection operations.

As described above, after the predetermined times of the detection operations are performed on the detection target pattern 33, the secondary electrons accumulated in the detection target pattern 33 may be saturated or reduced. Thus, the number of detection operations, which have been performed until the maximum secondary electron amount of the detection target pattern is obtained, may be determined from the N times detection operations (S300), such that the detection condition of the determined detection operation may be applied to mass production substrates. As a result, reliability of the semiconductor device inspecting method may be improved.

An experiment was performed using a method according to some embodiments of the inventive concept. The experiment was performed using the step S200 of the embodiment described with reference to FIGS. 10 and 11. The number of the pixel regions in the frame region FM was 60 in the experiment. The scan process was repeatedly performed six times in the experiment. The reference pattern 30 was the opened contact hole and the detection target pattern 33 was the not-opened contact hole.

Figure 16:
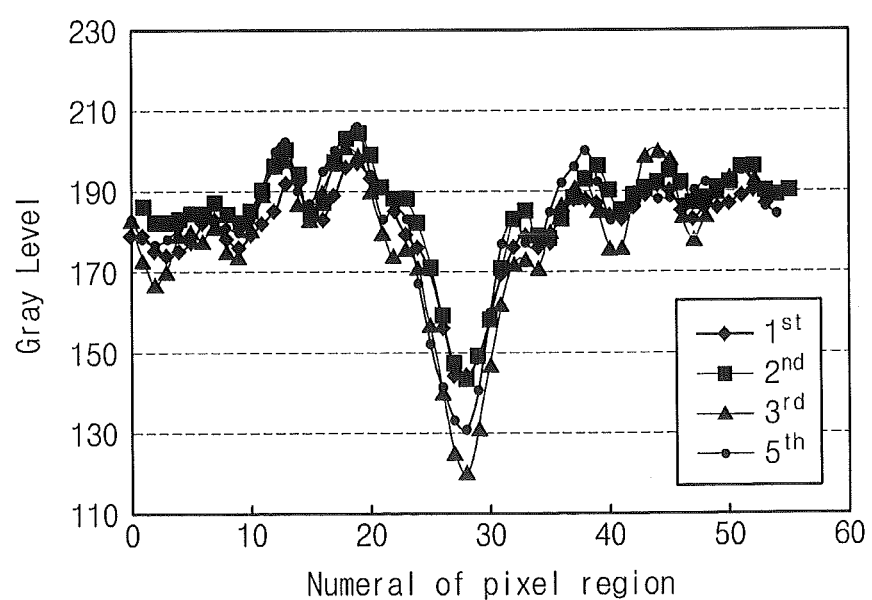
FIGS. 16 and 17 are graphs of grey levels of pixel regions and differences in the gray levels respectively obtained by a method of inspecting a semiconductor device according to some embodiments of the inventive concept.

FIG. 16 is a graph of grey levels of pixel regions obtained by a method of inspecting a semiconductor device according to some embodiments of the inventive concept.

Referring to FIGS. 11 and 16, the secondary electron amounts detected by the experiment were converted into gray levels, and then the gray levels were illustrated in the graph of FIG. 16. The detected secondary electron amount is reversely proportional to the gray level. As illustrated in FIG. 16, the not-opened contact hole (i.e., the detection target pattern) was disposed in a 28-th pixel region.

As illustrated in FIG. 16, the gray level of the not-opened contact hole obtained in a third scan process was less than the gray level of the not-opened contact hole obtained in a first scan process. In other words, the secondary electron amount of the not-opened contact hole obtained in the third scan process was greater than the secondary electron amount of the not-opened contact hole obtained in the first scan process. However, the gray level of the not-opened contact hole of a fifth scan process was greater than the gray level of the not-opened contact hole of the third scan process. In other words, the secondary electron amount of the not-opened contact hole of the fifth scan process was less than the secondary electron amount of the not-opened hole of the third scan process. Thus, the third scan process includes the detection operation from which the maximum secondary electron amount is obtained.

Figure 17:
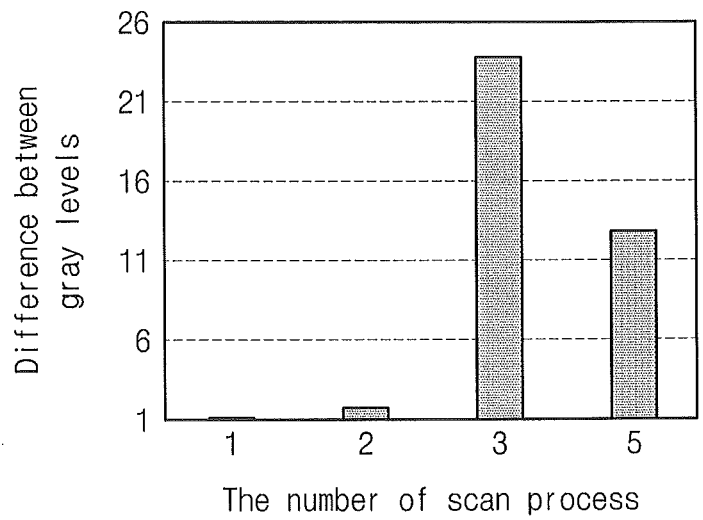

The gray level values were processed to obtain a graph of FIG. 17. FIG. 17 is a graph of differences in the gray levels respectively obtained from the grey levels of the pixel regions in FIG. 16.

Referring to FIG. 17, a y-axis of a graph represents differences between the obtained gray levels of the not-opened contact hole in the first scan process and the not-open contact holes in the rest scan processes. As illustrated in FIG. 17, the difference between the gray level of the third scan process and the gray level of the first scan process was the maximum value.

As described above, the number of detection operations, which have been performed until a maximum secondary electron amount of the detection target pattern is obtained, may be applied to mass production substrates. This will be described with reference to FIG. 18.

Figure 18:
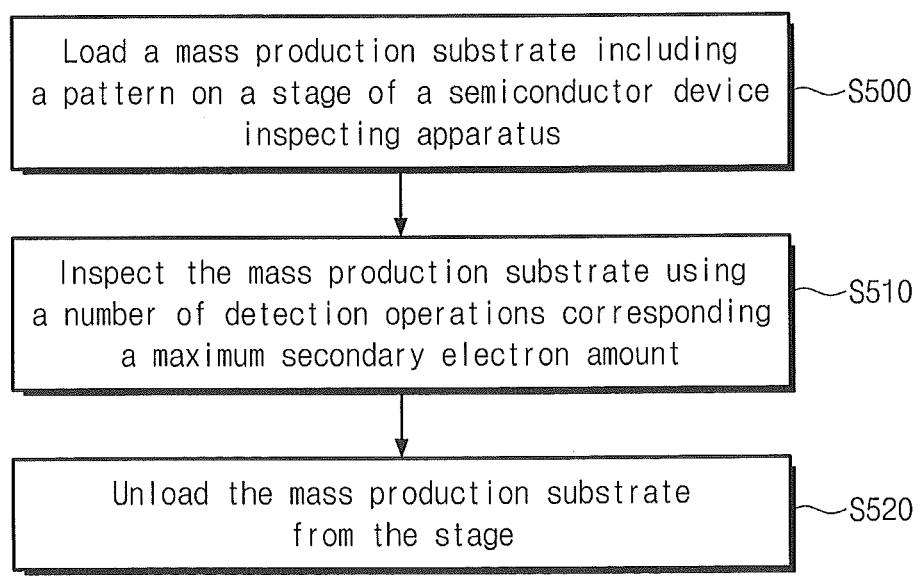
FIG. 18 is a flowchart illustrating a method of inspecting a mass production substrate according to some embodiments of the inventive concept.

FIG. 18 is a flowchart illustrating a method of inspecting a mass production substrate according to some embodiments of the inventive concept.

Referring to FIGS. 3 and 18, a mass production substrate including patterns is loaded on the stage 400 of the semiconductor device inspecting apparatus (S500).

The patterns of the mass production substrate are inspected using a number of detection operations corresponding a maximum secondary electron amount (S510). In some embodiments, if the step S200 described with reference to FIG. 10 is applied and the maximum secondary electron amount of the detection target pattern 33 is obtained in a M-th scan process, the scan process may be repeatedly performed M times on the frame region of the mass production substrate to inspect the mass production substrate. Here, 'M' denotes a natural number equal to or greater than 2 and equal to or less than N (N≥M≥2). In some embodiments, if the step S200 described with reference to FIG. 14 is applied and the maximum secondary electron amount of the detection target pattern 33 is obtained in a M-th detection operation (N≥M≥2), the detection operation may be repeatedly performed M times on each of the pixel regions of the mass production substrate to inspect the mass production substrate.

After the mass production substrate is inspected (S510), the mass production substrate is unloaded from the stage 400 of the semiconductor device inspecting apparatus (S520).

As described above, the detection operation using the reference electron-decay time RT is performed N times on the detection target pattern 33, and a number of detection operations, which have been performed until a maximum secondary electron amount of the detection target pattern is obtained, is determined from the N times of the detection operations. The number of detection operations, which have been performed until a maximum secondary electron amount of the detection target pattern is obtained, may be applied to the mass production substrate, such that reliability of the method of inspecting the mass production substrate may be improved.

According to the aforementioned semiconductor device inspecting methods of the inventive concept, the detection operation using the reference electron-decay time may be performed on the detection target pattern N times, and then the detection operation of the maximum secondary electron amount may be determined. The condition of the determined detection operation may be applied to the mass production substrate, such that the reliability of the inspecting method of the mass production substrate may be improved.

Additionally, the semiconductor device inspecting apparatus according to some embodiments may include the detector capable of continuously detecting the secondary electron amount of the pattern in real-time. Thus, the reference electron-decay time of the reference pattern and/or the electron-decay time of the detection target pattern may be easily obtained.

The above-disclosed subject matter is to be considered illustrative, and not restrictive, and the appended claims are intended to cover all such modifications, enhancements, and other embodiments, which fall within the true spirit and scope of the inventive concept. Thus, to the maximum extent allowed by law, the scope is to be determined by the broadest permissible interpretation of the following claims and their equivalents, and shall not be restricted or limited by the foregoing detailed description.

What is claimed is:

1. A method of inspecting a semiconductor device, the method comprising:
   obtaining a reference electron-decay time of a reference pattern that comprises a normal structure, the normal structure comprising a first conductive pattern that is substantially free of insulating residue;
   performing detection operations on a detection target pattern a number of times;
   obtaining an electron-decay time of the detection target pattern,
   wherein the detection target pattern comprises an abnormal structure that comprises a second conductive pattern including insulating residue therein,
   wherein each of the detection operations courses irradiating an electron beam to the detection target pattern, interrupting the electron beam for the reference electron-decay time and detecting a secondary electron amount of the detection target pattern at or after the reference electron-decay time has elapsed since the interrupting the electron beam,
   wherein the electron-decay time of the detection target pattern is greater than the reference electron-decay time of the reference pattern, and wherein a detection waiting time, which is a time interval between interrupting an electron beam and detecting a secondary electron amount of the detection target pattern in each of the detection operations, is less than the electron-decay time of the detection target pattern; and
   determining a number of detection operations which have been performed until a maximum secondary electron amount of the detection target pattern is obtained.

2. The method of claim 1, wherein a time interval between detecting a secondary electron amount of the detection target pattern of an i-th detection operation and a start of irradiating an electron beam to the detection target pattern of an (i+1)-th detection operation is less than a time interval between the electron-decay time of the detection target pattern and the detection waiting time.

3. The method of claim 2, wherein the detection waiting time is equal to the reference electron-decay time.

4. The method of claim 1, wherein obtaining the reference electron-decay time of the reference pattern comprises:
   irradiating an electron beam to the reference pattern;
   interrupting the electron beam; and
   continuously detecting a secondary electron amount of the reference pattern in real-time since a start of irradiating the electron beam.

5. The method of claim 4, wherein obtaining the reference electron-decay time of the reference pattern further comprises determining the reference electron-decay time of the reference pattern as a time that has elapsed until the secondary electron amount of the reference pattern becomes substantially zero or a noise signal level after interrupting the electron beam.

6. The method of claim 1, wherein obtaining the electron-decay time of the detection target pattern comprises:
   irradiating an electron beam to the detection target pattern;
   interrupting the electron beam; and
   continuously detecting a secondary electron amount of the detection target pattern in real-time since a start of irradiating the electron beam.

7. The method of claim 6, wherein obtaining the electron-decay time of the detection target pattern further comprises determining the electron-decay time of the detection target pattern as a time that has elapsed until the secondary electron amount of the detection target pattern becomes substantially zero or a noise signal level after interrupting the electron beam.

8. The method of claim 1, wherein the first conductive pattern comprises a first lower conductive pattern and a first upper conductive pattern that is electrically connected to and disposed on the first lower conductive pattern, and wherein the second conductive pattern comprises a second lower conductive pattern and a second upper conductive pattern that is disposed on the second lower conductive pattern, and the insulating residue is disposed between the second lower conductive pattern and the second upper conductive pattern.

9. The method of claim 1, wherein the first conductive pattern is disposed under a first contact hole and has an upper surface exposed by the first contact hole or the first conductive pattern is disposed in a second contact hole, and wherein the second conductive pattern is disposed under a third contact hole and has an upper surface on which the insulating residue is disposed or the second conductive pattern is disposed in a fourth contact hole and has a lower surface under which the insulating residue is disposed.

10. The method of claim 1, wherein performing the detection operations on the detection target pattern the number of times comprises:

performing scan processes the number of times on a frame region in a substrate, wherein the frame region comprises a plurality of pixel regions and one of the plurality of pixel regions includes the detection target pattern, and wherein each of the scan processes comprises detection operations on respective ones of the plurality of pixel regions.

11. The method of claim 10, wherein a scanning time interval between detecting a secondary electron amount of the one of the plurality of pixel regions of an i-th scan process and a start of irradiating an electron beam to the one of the plurality of pixel regions of an (i+1)-th scan process is less than a time interval between the electron-decay time of the detection target pattern and the reference electron-decay time, and wherein the electron-decay time of the detection target pattern is a time that has elapsed until the secondary electron amount of the detection target pattern becomes substantially zero or a noise signal level since interrupting the electron beam.

12. The method of claim 11, wherein the scanning time interval includes a frame movement time, an irradiation time obtained by multiplying a time during which an electron beam has been irradiated in each of the detection operations by a number of the pixel regions and a detection time obtained by multiplying the reference electron-decay time by the number of the pixel regions, and wherein the detection operations are performed by an inspecting head and the frame movement time is a movement time of the inspecting head.

13. The method of claim 10, wherein the plurality of pixel regions are two-dimensionally arranged along rows and columns in the frame region when viewed from a plan perspective.

14. The method of claim 10, wherein the plurality of pixel regions are arranged along one direction to constitute one row in the frame region when viewed from a plan perspective.

15. The method of claim 1, further comprising:
performing detection operations on a pattern in a mass production substrate the number of detection operations.

16. A method of inspecting an integrated circuit (IC) device, comprising:

determining a reference electron-decay time;
repetitively performing electron beam irradiation operations on a pattern in the IC device a number of times, each of the electron beam irradiation operations comprising irradiating the pattern with an electron beam for an irradiation time and interrupting the irradiating for the reference electron-decay time; and detecting a secondary electron amount of the pattern after a detection waiting time has elapsed since the repetitively performing the electron beam irradiation operations, wherein:

the pattern comprises a normal structure or an abnormal structure;

the normal structure comprises a first conductive pattern that is substantially free of insulating residue, and the abnormal structure comprises a second conductive pattern including insulating residue therein;

the detection waiting time is equal to or greater than the reference electron-decay time, and the electron beam remains interrupted for the detection waiting time; and determining the reference electron-decay time comprises:
irradiating a reference pattern with the electron beam for the irradiation time, wherein the reference pattern comprises the normal structure;
interrupting the irradiating after the irradiation time elapsed;
continuously detecting a secondary electron amount of the reference pattern since a start of the irradiating; and
determining the reference electron-decay time as a time for the secondary electron amount of the reference pattern to become substantially zero or less than a magnitude of a noise signal after the interrupting the irradiating.

17. The method of claim 16, further comprising determining an electron-decay time, wherein the detection waiting time is less than the electron-decay time.

18. The method of claim 17, wherein determining the electron-decay time comprises:

irradiating a target pattern with the electron beam for the irradiation time, wherein the target pattern comprises the abnormal structure;
interrupting the irradiating after the irradiation time elapsed;
continuously detecting a secondary electron amount of the target pattern since a start of the irradiating; and
determining the electron-decay time as a time for the secondary electron amount of the target pattern to become substantially zero or less than a magnitude of a noise signal after the interrupting the irradiating.

19. The method of claim 16, further comprising:
repetitively performing detection operations on a target pattern to provide respective secondary electron amounts of the target pattern, wherein:
the target pattern comprises the abnormal structure; and
each of the detection operations comprises irradiating the target pattern with the electron beam, interrupting the irradiating and detecting a secondary electron amount of the target pattern at or after the reference electron-decay time has elapsed since the interrupting the irradiating, wherein the electron beam remains interrupted until detecting the secondary electron amount of the target pattern in each of the detection operations; and
determining the number of times as a number of detection operations that have been performed when a maximum secondary electron amount of the target pattern is obtained.

20. A method of inspecting an integrated circuit (IC) device, comprising:
- determining a reference electron-decay time;
- determining an electron-decay time;
- repetitively performing detection operations on a target pattern in a substrate to provide respective secondary electron amounts of the target pattern,
- wherein the target pattern comprises an abnormal structure that comprises a conductive pattern including insulating residue therein, and
- wherein each of the detection operations comprises irradiating the target pattern with an electron beam, interrupting the irradiating for the reference electron-decay time, and detecting a secondary electron amount of the target pattern after a detection waiting time has elapsed since the interrupting the irradiating; and
- determining a number of detection operations that have been performed until a maximum secondary electron amount of the target pattern is obtained,
- wherein the detection waiting time is equal to or greater than the reference electron-decay time and is less than the electron-decay time.

21. The method of claim 20, wherein the conductive pattern comprises a first conductive pattern, and determining the reference electron-decay time comprises:
- irradiating a reference pattern with the electron beam for an irradiation time, wherein the reference pattern comprises a normal structure, and the normal structure comprises a second conductive pattern that is substantially free of insulating residue;
- interrupting the irradiating after the irradiation time elapsed;
- continuously detecting a secondary electron amount of the reference pattern since a start of the irradiating; and
- determining the reference electron-decay time as a time for the secondary electron amount of the reference pattern to become substantially zero or less than a magnitude of a noise signal after the interrupting the irradiating.

22. The method of claim 20, wherein the target pattern comprises a first target pattern comprising a first abnormal structure that comprises a first conductive pattern including first insulating residue therein, and determining the electron-decay time comprises:

- irradiating a second target pattern with the electron beam for an irradiation time, wherein the second target pattern comprises a second abnormal structure that comprises a second conductive pattern including second insulating residue therein;
- interrupting the irradiating after the irradiation time elapsed;
- continuously detecting a secondary electron amount of the second target pattern since a start of the irradiating; and
- determining the electron-decay time as a time for the secondary electron amount of the second target pattern to become substantially zero or less than a magnitude of a noise signal after the interrupting the irradiating.

23. The method of claim 20, wherein the target pattern comprises a first target pattern comprising a first abnormal structure that comprises a first conductive pattern including first insulating residue therein, a time interval between detecting a secondary electron amount of the target pattern of an i-th detection operation and a start of irradiating an electron beam to the target pattern of an (i+1)-th detection operation is less than a time interval between the electron-decay time and the detection waiting time, and wherein determining the electron-decay time comprises:

- irradiating a second target pattern with the electron beam for an irradiation time, wherein the second target pattern comprises a second abnormal structure that comprises a second conductive pattern including second insulating residue therein;
- interrupting the irradiating after the irradiation time elapsed;
- continuously detecting a secondary electron amount of the second target pattern since a start of the irradiating; and
- determining the electron-decay time as a time for the secondary electron amount of the second target pattern to become substantially zero or less than a magnitude of a noise signal after the interrupting the irradiating.

24. The method of claim 20, further comprising performing detection operations on a pattern in a mass production substrate the number of detection operations.

* * * * *